(12) United States Patent
Tulip

(10) Patent No.: US 6,750,467 B2
(45) Date of Patent: Jun. 15, 2004

(54) VEHICLE MOUNTED GAS DETECTOR

(76) Inventor: John Tulip, 11625 Edinboro Road, Edmonton Alberta (CA), T6G 1Z7

(*) Notice: Subject to any disclaimer, the term of this patent is extended or adjusted under 35 U.S.C. 154(b) by 2 days.

(21) Appl. No.: 10/143,828

(22) Filed: May 14, 2002

(65) Prior Publication Data

US 2003/0213912 A1 Nov. 20, 2003

(51) Int. Cl.$^7$ .............................................. G01N 21/85

(52) U.S. Cl. ........................ 250/573; 250/574; 356/437

(58) Field of Search ............................ 250/221, 222.1, 250/573–574, 388.5, 339.13, 343; 340/603, 605, 540, 637; 356/437

(56) References Cited

U.S. PATENT DOCUMENTS

| | | | |
|---|---|---|---|
| 4,410,271 A | 10/1983 | Matthews | 356/301 |
| 4,489,239 A | 12/1984 | Grant et al. | 250/339 |
| 4,543,481 A | 9/1985 | Zwick | 250/339.03 |
| 4,953,976 A | 9/1990 | Adler-Golden et al. | 356/301 |
| 5,173,749 A | * 12/1992 | Tell et al. | 356/437 |
| 5,202,570 A | 4/1993 | Tanaka et al. | 250/575 |
| 5,255,073 A | 10/1993 | Wallin et al. | 356/437 |
| 5,267,019 A | 11/1993 | Whittaker et al. | 356/437 |
| 5,485,276 A | * 1/1996 | Bien et al. | 356/437 |
| 5,637,872 A | 6/1997 | Tulip | 250/338.5 |

FOREIGN PATENT DOCUMENTS

| | | | | |
|---|---|---|---|---|
| CA | PCT/CA96/00385 | 6/1996 | | F17D/5/02 |
| CA | 2219335 | 11/1997 | | B64D/47/00 |
| FR | 2815122 A1 | * 4/2002 | | G01N/21/17 |
| GB | PCT/GB88/00776 | 9/1988 | | G01N/21/39 |

OTHER PUBLICATIONS

"Diode lasers finding trace gases in the lab and the plant", David Bomse, Photoncs Spectra, Jun., 1995, p. 88–93.

"Diode laser spectroscopy for gas monitoring of environmental pollution and for industrial process and emission control", Åse Margrete Ballangrud, A thesis submitted to the University of Oslo in partial fulfilment of the requirements for the degree Dr. Scient, Jun., 1993, Chapters 5, 6, and 8.

"In situ and real–time measurement of methane concentration in rice paddy field at Okayama University using tunable diode laser adsorption spectrometry", Naoki Kagawa, Osami Wada, Xu Hai, Ryuji Koga, Hiroya Sano and Kazayuki Inubushi, Jpn. J. Appl. Phys. vol. 32 (1993)Pt. 1, No. 1A, p. 244–245.

"Environmental monitoring of gases using near–infrared diode lasers", by David Bomse, Optics & Photonic News, Sep., 1996, 4 pages.

"Mid–Infrared tunable laser environmental tracer species measurement", by C.E. Holb, J.B. McManus, D.D. Nelson, J.C. Wormhoudt, and M.S. Zahniser, Optics & Photonic News, Sep., 1996, 5 pages.

Boreal Laser Inc. Technical Information, first distributed Oct. 28, 1996, 2 pages.

(List continued on next page.)

Primary Examiner—David Porta
Assistant Examiner—Patrick J. Lee
(74) Attorney, Agent, or Firm—Anthony R. Lambert

(57) ABSTRACT

A mobile gas detector comprising a laser transmitter and signal analyser carried on a vehicle, the vehicle having an exterior, a laser absorption cell carried on the exterior of the vehicle, a light guide connecting light from the laser transmitter into the laser absorption cell, a photo-detector mounted with the laser absorption cell exterior to the vehicle to convert light that has traversed the laser absorption cell into electrical signals, and a cable connecting the photodetector to the signal analyser.

20 Claims, 3 Drawing Sheets

OTHER PUBLICATIONS

"Airborne lasers accurately measure greenhouse gases", Glen W. Sachse and Edward V. Browell, Laser Focus World, Apr., 1997, 2 pages.

"Aircraft (ER–2) laser infrared adsorption spectrometer (ALIAS) for in–situ stratospheric measurements of HCl, $N_2O$, $CH_4$, $NO_2$, and $HNO_3$", C.R. Webster, R.D. May, C.A. Trimble, R.G. Chave, and J. Kendall, Applied Optics, vol. 33, No. 3, Jan. 20, 1994, p. 454–468.

"Remote detection of gases by diode laser spectroscopy", A. Mohebati and T.A. King, Journal of Modern Optics, vol. 35, No. 3, 1988, 319–324.

"A novel optical fibre methane sensor", J.P. Dakin, C.A. Wade, D. Pinchbeck, and J.S. Wykes, SPIE vol. 374, Fibre Optics '87: Fifth International Conference on Fibre Optics and Opto–Electronics, 1987, 254–260.

"Remote detection of methane with a 1.66–$\mu$m diode laser", Kiyoji Uehara and Hideo Tai, Applied Optics, vol. 31, No. 6, Feb. 1992, 809–814.

\* cited by examiner

US 6,750,467 B2

VEHICLE MOUNTED GAS DETECTOR

FIELD OF THE INVENTION

This invention relates to vehicle mounted gas detectors using laser absorption cells.

BACKGROUND OF THE INVENTION

Vehicle mounted gas sensors pose difficult problems not found with stationary sensors. In particular, for aircraft mounted gas sensors the difficult environmental conditions make accurate and reliable measurement difficult. Aircraft and other fast moving vehicles are subject to mechanical disturbance such as from rapid temperature variations, from −50° C. to 30° C., high wind speed, high vibrations and impact from fast moving objects, including birds, flies, ice pellets, rain and snow. Aircraft, other fast moving vehicles and in particular helicopters are also subject to electrical interference. The design of a robust and sensitive mobile gas sensor poses a difficult design challenge.

Canadian patent application no. 2,219,335 published Nov. 24, 1997 shows a prior art laser absorption cell for a gas detector. The gas detector is designed for use with aircraft and has a laser absorption cell of the Herriot type carried on the exterior of the aircraft. This laser absorption cell was used for example to detect methane leaks from pipelines. A laser transceiver and analyser module mounted on board the aircraft is coupled to the laser absorption cell through multi-mode fiber optics. Use of multi-mode fiber optics caused optical noise and reduced detection sensitivity. To reduce optical noise, detection of methane took place in the 1300 nm absorption wavelength since that wavelength was less affected by the telecommunication fiber optic. However, since absorption of light in the methane absorption band at 1300 nm is relatively weak, multiple passes of the Herriot cell were required to obtain a suitable strong signal. Due to the multiple passes of light across the Herriot cell, and the necessity of collimating the light into an optical fiber for delivery of light to the laser receiver, the gas detector was sensitive to thermal and mechanical misalignment that decreased the detector's reliability and required high maintenance. Reduced reliability and high maintenance of the gas detector restricted its use to the rental market.

SUMMARY OF THE INVENTION

To overcome problems of the prior art gas detector, a gas detector is now proposed according to an aspect of the invention that uses a photo-detector mounted with the laser absorption cell exterior to the vehicle to detect light that has made at least one pass of the laser absorption cell.

Therefore, there is provided, according to an aspect of the invention, a laser transmitter and signal analyser carried on, and preferably within, a vehicle, the vehicle having an exterior, a laser absorption cell carried on the exterior of the vehicle, a light guide connecting light from the laser transmitter into the laser absorption cell, a photo-detector mounted with the laser absorption cell exterior to the vehicle to convert light that has traversed the laser absorption cell into electrical signals, and a cable connecting the photo-detector to the signal analyser.

According to a further aspect of the invention, there is provided a method of detecting a target gas, the method comprising the steps of:

traversing a target area with a vehicle having an exterior;

passing air through a laser absorption cell carried on the exterior of the vehicle;

directing light through the laser absorption cell;

converting light that has made at least one pass through the laser absorption cell into electrical signals using a photo-detector mounted with the laser absorption cell exterior to the vehicle; and analysing the electrical signals for a signal indicative of the presence of the target gas.

According to a further aspect of the invention, a laser absorption cell, in which light emitted from a light guide traverses the cell and is collected by a photo-detector, is provided with a retro-reflector to reflect light that has entered the light absorption cell from the light guide towards the photo-detector. The retro-reflector accommodates misalignment of the light guide and photo-detector in the high vibration environment of a fast moving vehicle.

According to a further aspect of the invention, a mirror is mounted on the frame to reflect light from the light guide across the light absorption cell in at least two back and forth passes before the light reaches the photo-detector.

According to a further aspect of the invention, the gas detector further comprises a protective window mounted on the frame over the retro-reflector to protect the retro-reflector from airborne contaminants.

In one optical arrangement, light from the light guide traverses the laser absorption cell reflected off a mirror across the cell, and is directed onto the photo-detector, for example by a collecting mirror such as an offset parabolic mirror.

In another optical arrangement, light from the light guide traverses the laser absorption cell to a retro-reflector and reflected from the retro-reflector onto a photo-detector.

The mobile gas detector is primarily used for airborne detection. Use of a photo-detector allows detection of methane using light within the methane absorption band at 1650 nm. The photo-detector is preferably a photo-diode operating in photo-voltaic mode to avoid the need for an external power supply for the photo-detector.

These and other aspects of the invention are described in the detailed description of the invention and claimed in the claims that follow.

BRIEF DESCRIPTION OF THE DRAWINGS

There will now be described preferred embodiments of the invention, with reference to the drawings, by way of illustration only and not with the intention of limiting the scope of the invention, in which like numerals denote like elements and in which.

DETAILED DESCRIPTION OF PREFERRED EMBODIMENTS

In this patent document, "comprising" is used in its inclusive sense, and does not exclude other elements being present. In addition, the use of the indefinite articles "a" or "an" does not exclude more than one of the elements referred to being present. "Light" means electromagnetic radiation having a wavelength that is suited to the detection of gas. A "light guide" is any device suitable for guiding light, such as a waveguide, optical fiber or lens arrangement. A "retro-reflector" is a reflector that reflects light back to its source.

Figure 1:
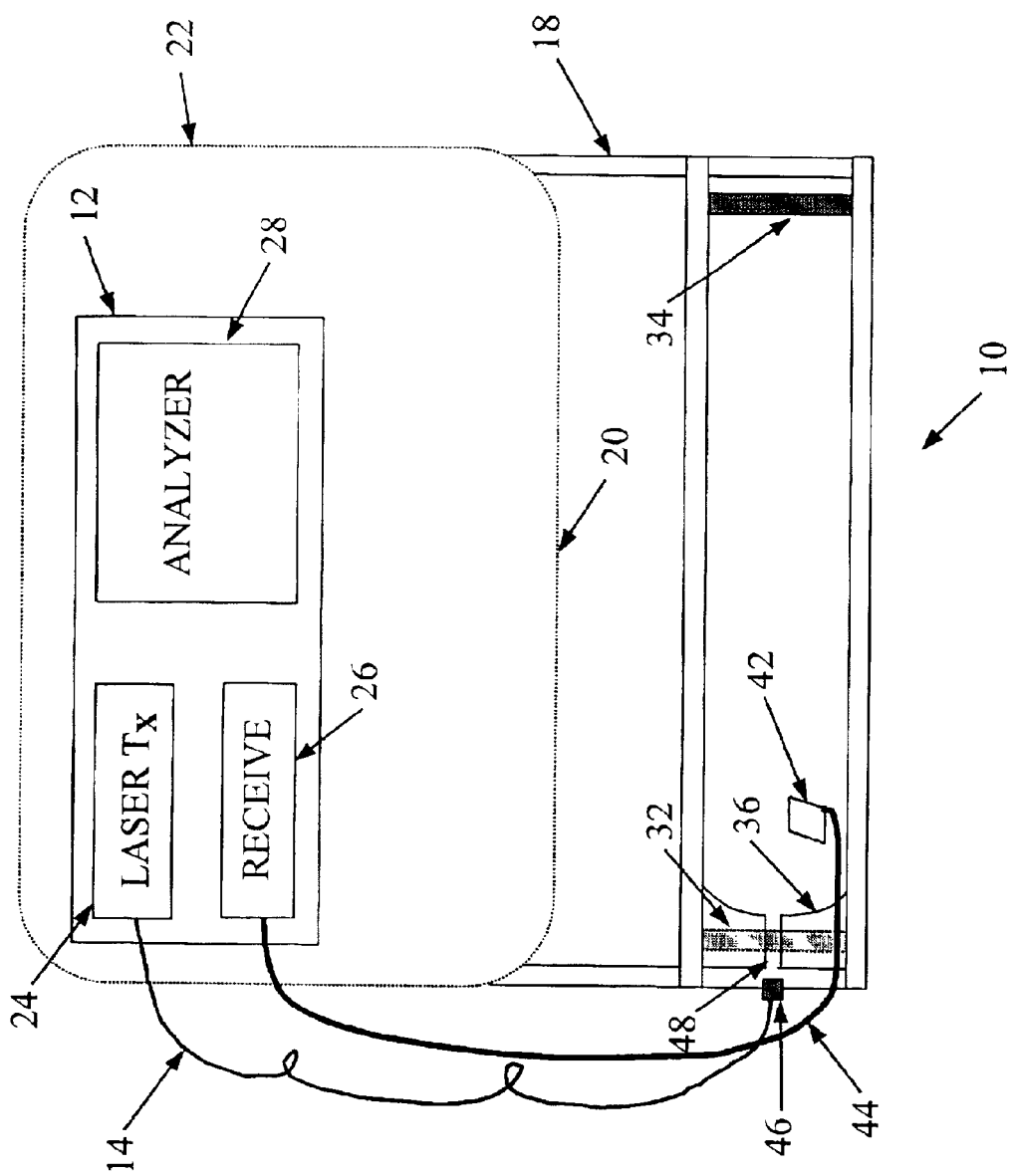
FIG. 1 is a diagram showing an exemplary installation of a laser absorption cell according to the invention.

The gas detector of the invention is intended for mounting on a vehicle, such as a motor vehicle, aircraft or ship. The gas detector is formed of a laser absorption cell 10, a laser transmitter, receiver and analyser module 12 and a light guide 14 and coaxial cable 44 connecting the module 12 and cell 10. Advantageously, the laser absorption cell 10 of the gas detector is mounted on the exterior of the vehicle, for example using a frame 18 slung under the belly 20 of a helicopter 22, while the laser transmitter, receiver and analyser module 12 is carried on the vehicle, and preferably in the vehicle 22 as shown in FIG. 1 for access by an operator. The frame 18 defines a passageway through which air flows as the aircraft flies, for example, along a pipeline. The module 12 incorporates a laser transmitter 24, receiver 26 and analyser 28. The laser transmitter 24 may be for example a conventional telecommunications diode laser with output at 1650 nm, such as are available from NEL (Nippon Electro-optical Lasers) of Japan.

The laser transmitter 24 is optically coupled to the laser absorption cell 10 by a light guide 14, which delivers light to the laser absorption cell 10. The receiver 26 and analyser 28 each incorporate conventional electronics for receiving and analysing electrical signals that are indicative of light that has passed through a target gas. Use of the stronger 1650 nm absorption band of methane permits the cell 10 to have a shorter path length than the prior art absorption cell described in Canadian patent application 2,219,335, with the width of the cell 10 between the retro-reflector 32 and the mirror 34 being in the order of 60 cm for example.

Figure 2:
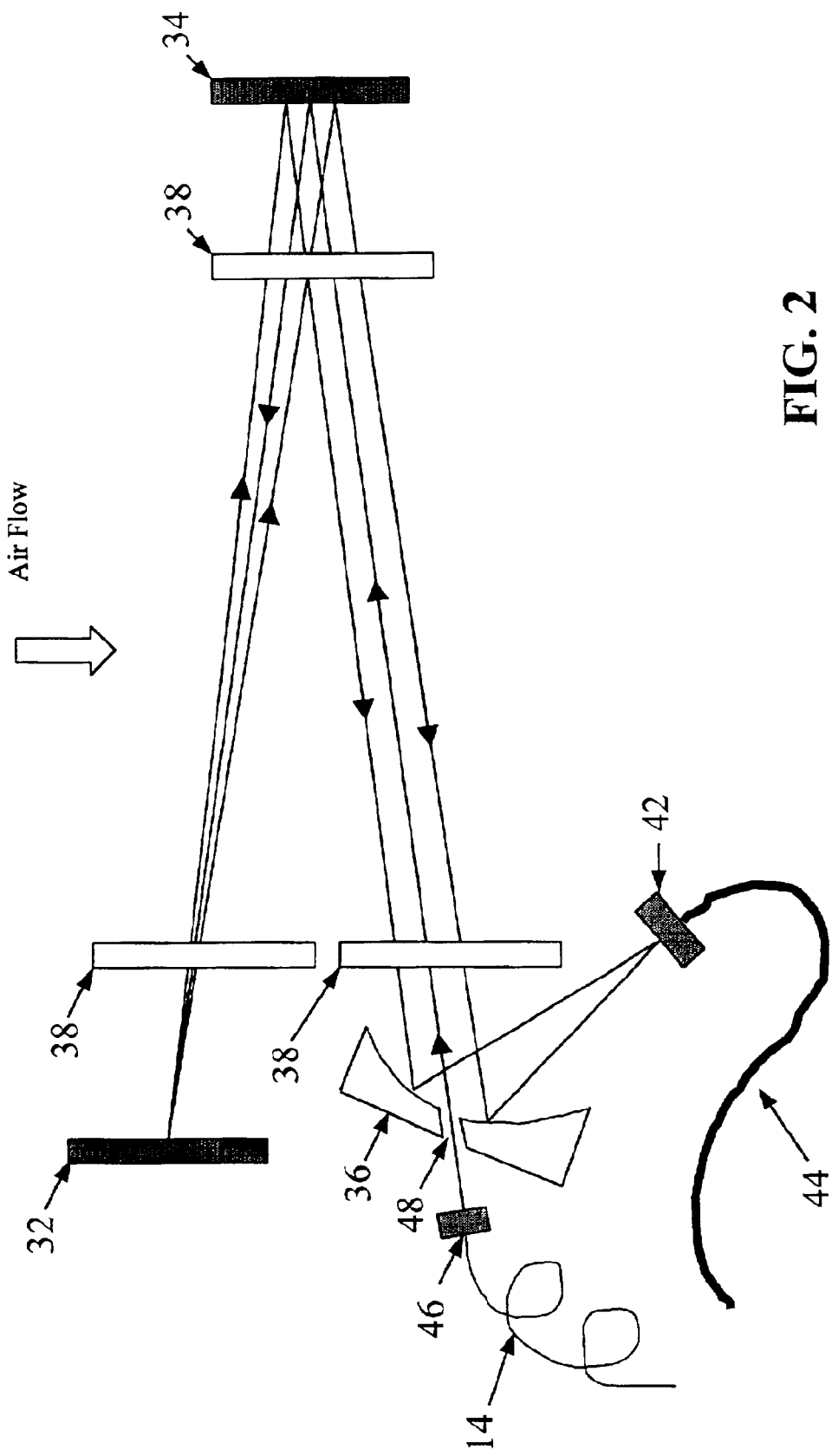
FIG. 2 is a schematic showing the principles of operation of an exemplary laser absorption cell according to the invention.

As shown in FIG. 2, an exemplary laser absorption cell 10 is formed of retro-reflector 32, such as made from retro-reflective tape, mounted on one side of the frame 18, a mirror 34 on the other side of the frame 18, a collecting mirror 36 and protective windows 38 for each of the retro-reflective tape 32 and minors 34 and 36. Air flows between the mirrors 34 and 36 as indicated by the arrow. The retro-reflector 32 is preferably of the type typically used by construction crews and has the property that light incident on the tape 32 is reflected back along the incident ray path. A light guide 14 connects light from the laser transmitter 24 into the laser absorption cell 10. Use of the photo-detector 42 permits use of a single mode optical fiber as the light guide 14 such as is available from Corning Inc. of Corning, N.Y. instead of the multi-mode return fiber used in the prior art. A photo-detector 42 is mounted on the frame 18 with the laser absorption cell 10 and exterior to the vehicle to convert light that has traversed the laser absorption cell 10 into electrical signals. Light from the cell 10 is focused onto the photo-detector 42 with collecting mirror 36. A coaxial cable 44 connects the photo-detector 42 to the signal analyser 28 through the receiver 26. Light is input to the laser absorption cell 10 through a collimating lens 46 also mounted with the laser absorption cell 10 on the frame 18.

Since the laser absorption cell 10 is intended to be operated in hazardous areas, and could be moved through a cloud of explosive gas, the photo-detector 42 should be electrically safe, and for example should not require an external power source. One manner of operating the photo-detector 42 in an electrically safe manner is to operate the photo-detector 42 in photo-voltaic mode, which produces very small, but detectable, electrical signals in the coaxial cable. The photo-detector 42 may be for example a commercially available Indium-Gallium-Arsenide photo-diode. To avoid capacitance between the photo-detector 42 and the receiver 24, the photo-detector 42 is connected with a parallel 50 ohm resistor to the coaxial cable 44. This reduces electrical interference from the vehicle and helps make the electrical arrangement electrically safe.

Windows 38 may be used to protect the reflector 32 and mirrors 34, 36 from contamination from material carried by air passing through the cell. The windows 36 are secured on the frame 18 adjacent the reflector 32 and mirrors 34, 36. The windows 38 are preferably made of scratch resistant low interference material such as 0.5 mm thick sapphire sheets, as are typically used with lasers at checkout counters of retail stores. The frame 18 may be made of steel rods arranged at three of the four corners of a square. The collecting mirror 36 is preferably an offset parabolic nearly 100% reflecting mirror, and may be obtained from Jason Optics. An offset parabolic mirror has the desirable property that it is insensitive to misalignment. An equivalent lens could be used for the collecting optic, but a lens is less desirable due to greater optical noise. The mirror 34 is a plane nearly 100% reflecting mirror. Mirror 36 has a hole or opening 48 in it for allowing light from the collimating optic 46 into the cell 10. The mirror 36 should be large enough to accommodate any beam misalignment and direct the light onto the photo-detector over a range of incident angles of the light traversing the cell caused for example by misalignment of the optical components and vibrations.

The frame 18 is arranged with two upper rods located close to the vehicle, one being forward of the other in the direction of movement of the vehicle during gas detection. The third rod is mounted below the rearward rod. The rods are spaced apart, and together with the mirrors, form a passageway through the cell 10 as indicated by the arrow. A conduit is not required to supply air to the laser absorption cell, and the passageway thus preferably provides direct flow of air through the cell 10 without alteration of the predominant flow direction of the air shown by the arrow. The entire cell 10 may be wrapped in a porous fabric that is attached by zips or Velcro™ fasteners like a sock around the cell 10. The fabric may for example be made of a nylon mesh outer shell and ½ inch low density foam rubber inner shell. At both ends of the cell 10, the sock may be made of a stiffer and non-porous fabric such as canvas to protect the optical components. The fabric keeps birds and flies out of the cell and reduces maintenance, without impeding air flow to an extent that it affects the response time of the detector.

The light path through the cell 10 shown in FIG. 2 passes across the cell in two double passes. The first double pass runs from the collimating optic across to the mirror 34 and then to the tape 32. The second double pass returns approximately along the path of the first double path, with divergence of the returning beam being accommodated by the collecting mirror 36.

The laser transmitter, receiver and analyser module 12 may be any of several laser transmitters, receivers and analysers known in the art. The inventor prefers to use the design for the receiver and analyser shown in his own U.S. Pat. No. 5,637,872 using the second harmonic. There are numerous other designs that could be used for the laser transceiver and analyser module, such as are referred to in U.S. Pat. No. 5,637,872.

In operation, an aircraft or other vehicle 22 traverses a target area, for example by flying along a pipeline, with a laser absorption cell 10 carried on the exterior of the helicopter, such that air passes through the passageway in the direction of the arrow. Light is transmitted by the laser transmitter 24 through the laser absorption cell 10 and returns to the photo-detector 42. The light that has passed through the laser absorption cell is then analysed in analyser 28 for absorption at one of the absorption bands of the target gas, which indicates the presence of the target gas.

The laser absorption cell disclosed here is stable, economical and requires very little maintenance. Since there are only two passes and the retro-reflector is independent of misalignment, no thermal correction means are required and protective windows may be used, which are easy to clean. The cell is not vulnerable to air turbulence misalignment so it is not necessary to protect the beam path, thus avoiding the drag created by the prior art laser absorption cell.

Figure 3:
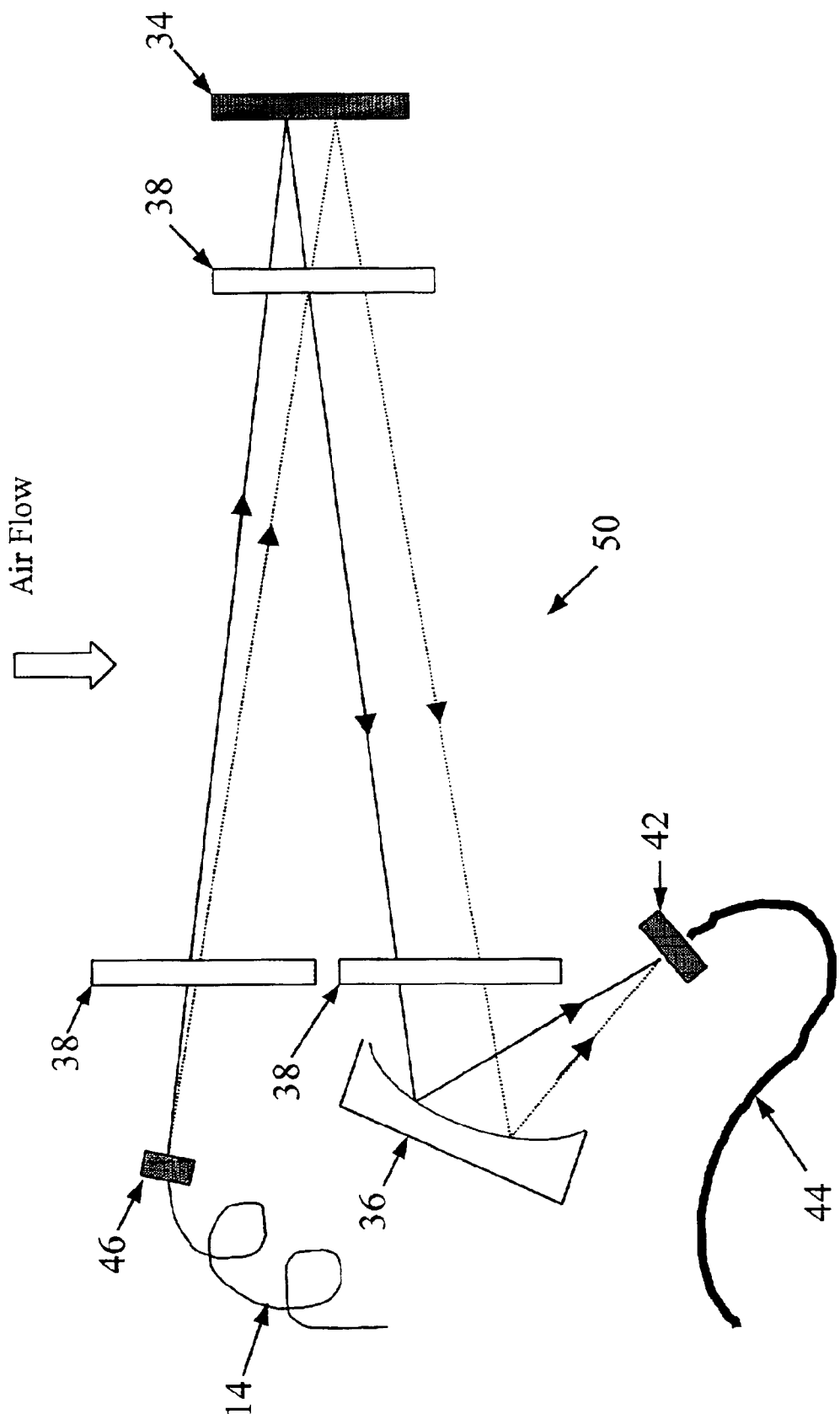
FIG. 3 is a schematic showing the principles of operation of a second exemplary laser absorption cell according to the invention.

An alternative embodiment is shown in FIG. 3, in which a single double pass is used. The lens 46 is placed to direct light across the cell 50 to the mirror 34, thence to the mirror 36, which directs light onto the photo-detector 42. The retro-reflector 32 is omitted. The figure shows two slightly misaligned paths, the divergence of which is accommodated by the collecting mirror 36.

Due to the need to precisely locate leaks when moving at high speed, readings should be taken at rates in the order of 100 times per second. To reduce the 1/f noise associated with these rates, the system should operate at high frequency, for example at 20 MHz.

A person skilled in the art could make immaterial modifications to the invention described in this patent document without departing from the essence of the invention that is intended to be covered by the scope of the claims that follow.

What is claimed is:

1. A mobile gas detector, comprising:
    a laser transmitter and signal analyser carried within a vehicle, the vehicle having an exterior;
    a laser absorption cell carried on the exterior of the vehicle;
    a light guide connecting light from the laser transmitter into the laser absorption cell;
    a photo-detector mounted with the laser absorption cell exterior to the vehicle to convert light that has traversed the laser absorption cell into electrical signals; and
    a cable connecting the photo-detector to the signal analyser.

2. The mobile gas detector of claim 1 in which the laser absorption cell comprises:
    a frame attached to the exterior of the vehicle, the frame having a passageway passing through the frame; and
    a retro-reflector oriented to reflect light t at has entered the light absorption cell from the light guide towards the photo-detector.

3. The mobile gas detector of claim 2 in which a mirror is mounted on the frame to reflect light from the light guide across the light absorption cell in at least two back and forth posses before the light reaches the photo-detector.

4. The mobile gas detector of claim 2 further comprising a protective window mounted on the frame over the retro-reflector to protect the intro-reflector from airborne contaminants.

5. The mobile gas detector of claim 1 in which the vehicle is a helicopter.

6. The mobile gas detector of claim 1 in which the laser transmitter transmits light in the 1650 nm absorption band of methane.

7. The mobile gas detector of claim 1 in which the photo-detector is operated in an electrically safe manner for explosive operating conditions.

8. The mobile gas detector of claim 1 in which the photo-detector is a photo-diode configured to operate in photo-voltaic mode.

9. The mobile gas detector of claim 1 in which the light guide and photo-detector are mounted on one side of the laser absorption cell, a mirror is mounted on an opposed side and the light guide is oriented to direct light across the laser absorption cell, reflect off the mirror, onto the photo-detector.

10. The mobile gas detector of claim 9 further comprising an offset parabolic mirror mounted on the frame to collect light that has traversed the laser absorption cell and direct the light onto the photo-detector.

11. A method of detecting a target gas, the method comprising the steps of:
    traversing a target area with a vehicle having an exterior;
    passing air through a laser absorption cell carried on the exterior of the vehicle;
    directing light through the laser absorption cell from a laser transmitter carried within the vehicle;
    converting light that has made at least one pass through the laser absorption cell into electrical signals using a photo-detector mounted with the laser absorption cell exterior or to the vehicle; and
    analysing the electrical signals for a signal indicative of the presence of the target gas.

12. The method of claim 11 in which the step of analysing the light is carried out in a signal analyser carried inside the vehicle.

13. The method of claim 11 in which the laser absorption cell is carried on an aircraft.

14. The method of claim 11 in which the light directed through the laser absorption cell is in the 1650 nm absorption band of methane.

15. The method of claim 11 in which the photo-detector operates in an electrically safe manner for an explosive operating environment.

16. The method of claim 11 in which the photo-detector is a photo-diode operating in photo-voltaic mode.

17. A mobile gas detector, comprising:
    a laser transmitter and signal analyser carried on a vehicle, the vehicle having an exterior;
    a laser absorption cell carried on the exterior of the vehicle, the laser absorption cell having a frame attached to the exterior of the vehicle, the frame having a passageway passing through the frame;
    a light guide connecting light from the laser transmitter into the laser absorption cell;
    a photo-detector mounted on the vehicle to convert light that has traversed the laser absorption cell into electrical signals;
    a cable connecting the photo-detector to the signal analyser; and
    a retro-reflector oriented on the frame to reflect light that has entered the light absorption cell from the light guide towards the photo-detector.

18. The mobile gas detector of claim 17 in which the retro-reflector is mounted on a side of the passageway opposed to the photo-detector.

19. The mobile gas detector of claim 17 in which the retro-reflector and the photo-diode are on the same side of the passageway.

20. The mobile gas detector of claim 17 in which the photo-detector is a photo-diode operating in photo-voltaic mode.

* * * * *